United States Patent [19]
Grieshaber et al.

[11] 4,087,878
[45] May 9, 1978

[54] TOOL CLEANING DEVICE

[76] Inventors: Herman R. Grieshaber, 621 Exmoor Rd., Kenilworth, Ill. 60043; Jack E. Wilkinson, 544 Fresno St., Fresno, Calif. 93706

[21] Appl. No.: 666,326

[22] Filed: Mar. 12, 1976

[51] Int. Cl.² ............................................. A46B 17/06
[52] U.S. Cl. .................................... 15/111; 15/104.92; 15/160; 15/218.1
[58] Field of Search ................. 15/21 D, 38, 39, 111, 15/114, 160, 210 R, 218.1, 104.92, 423; 128/2 B, 104.5–104.53

[56] References Cited

U.S. PATENT DOCUMENTS

| | | | |
|---|---|---|---|
| 177,394 | 5/1876 | Hall et al. | 15/218.1 |
| 885,497 | 4/1908 | Maibaum | 15/39 |
| 1,732,467 | 10/1929 | Gregory | 15/423 |
| 1,901,262 | 3/1933 | Robideau | 15/104 R X |
| 2,121,307 | 6/1938 | Swift | 15/39 X |
| 2,202,516 | 5/1940 | Calleo | 15/104.5 X |
| 2,744,276 | 5/1956 | Chambless | 15/104.92 |
| 3,428,988 | 2/1969 | Blackburn | 15/160 |
| 3,583,018 | 6/1971 | Fink | 15/104.92 |
| 3,761,984 | 10/1973 | Hauschild et al. | 15/39 X |

FOREIGN PATENT DOCUMENTS

| | | | |
|---|---|---|---|
| 975,037 | 10/1950 | France | 15/39 |
| 27,251 | 5/1884 | Germany | 15/423 |
| 57,351 | 8/1946 | Netherlands | 15/104.92 |
| 290,641 | 8/1928 | United Kingdom | 15/39 |

*Primary Examiner*—Peter Feldman
*Attorney, Agent, or Firm*—Neuman, Williams, Anderson & Olson

[57] ABSTRACT

A device is provided which is adapted for use in manually cleaning a segment of a surgical tool or instrument. The device includes a hollow casing having an elongated slot formed in a portion of the exterior surface thereof. The slot is adapted to have a segment of the tool inserted therethrough and then moved longitudinally of the slot. Disposed within the casing is a setose member having the setae thereof disposed adjacent to and aligned with said casing slot. The setae are resilient and frictionally engage the inserted tool segment when the latter is moved longitudinally of the slot.

4 Claims, 13 Drawing Figures

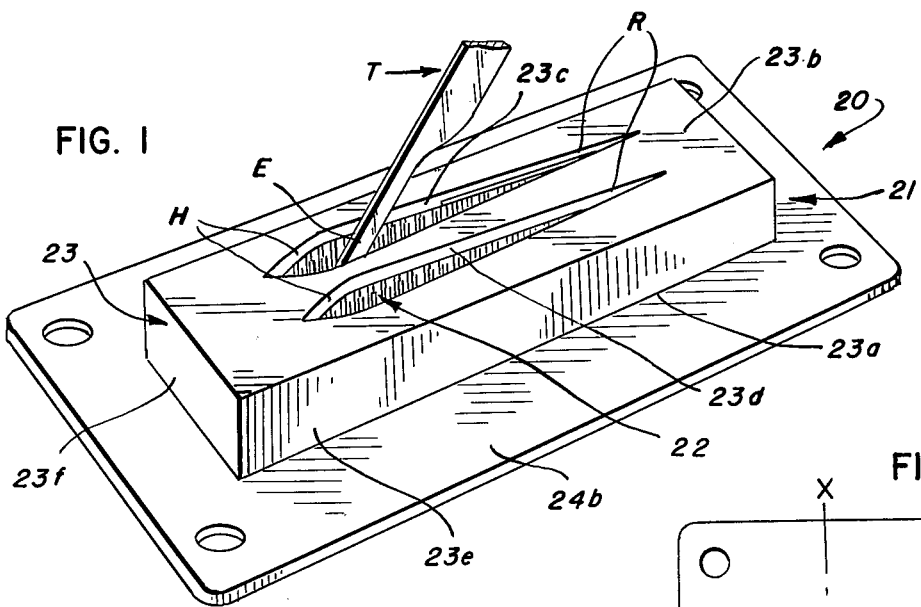
FIG. 1
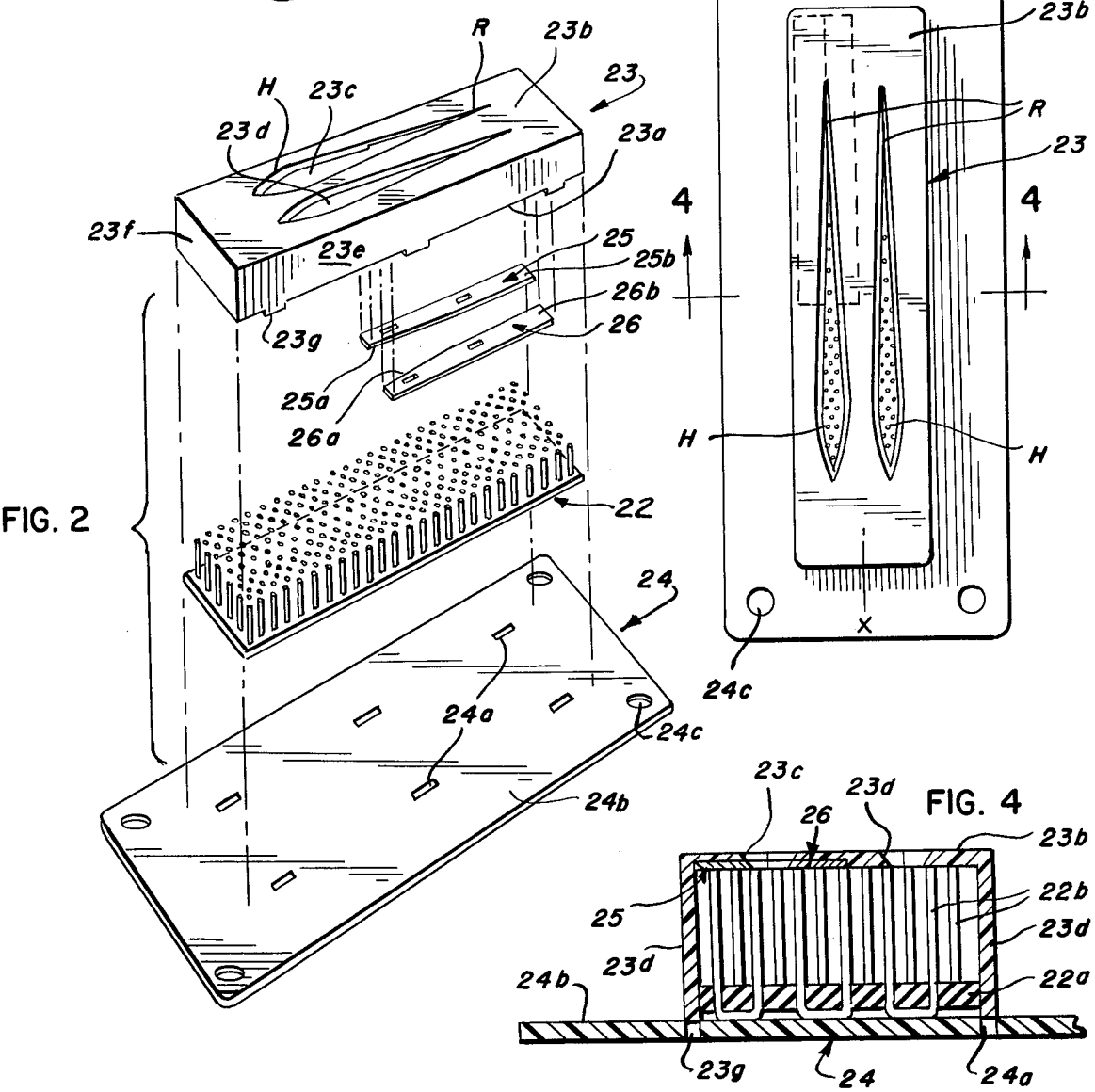
FIG. 2
FIG. 3
FIG. 4

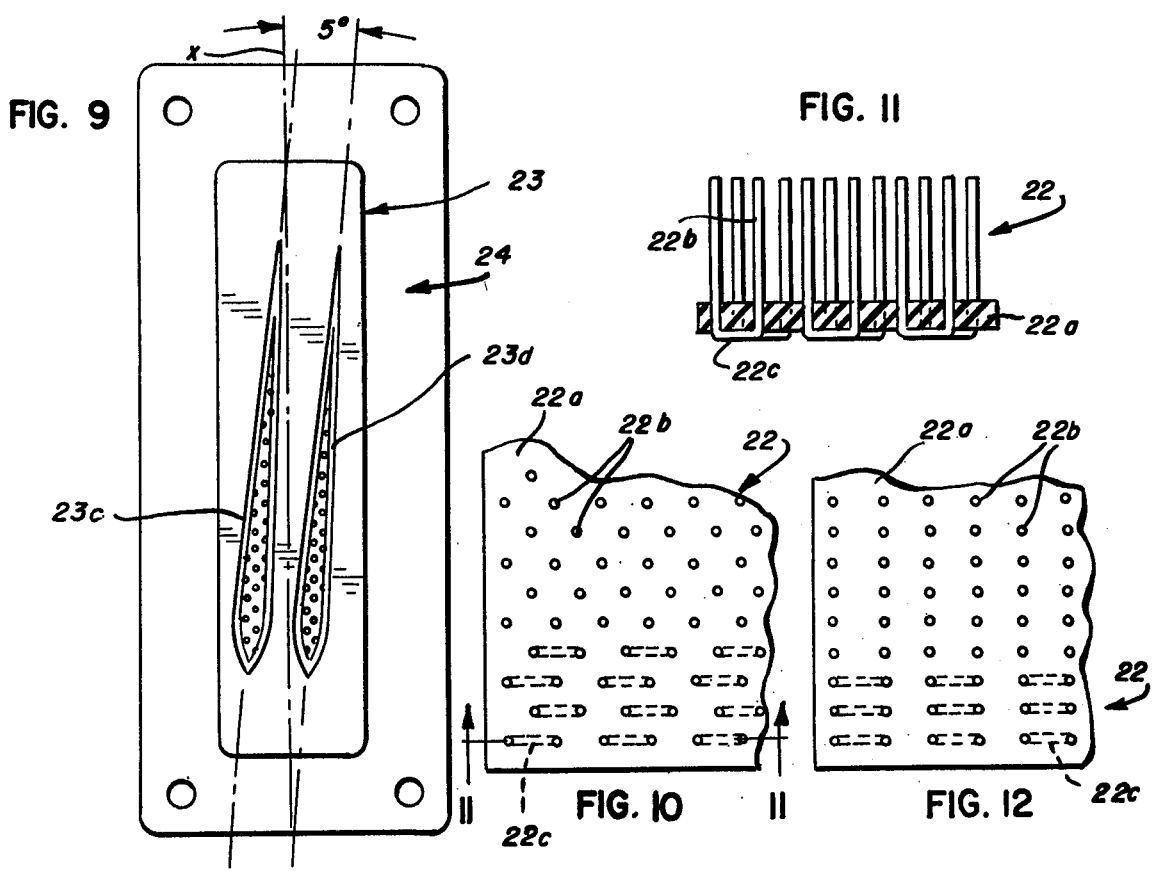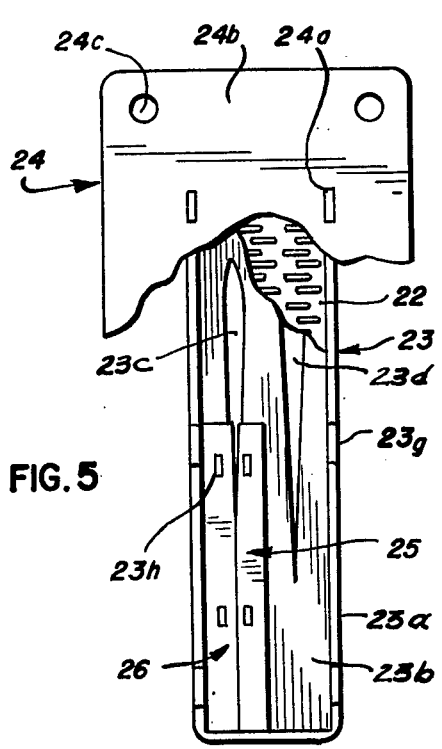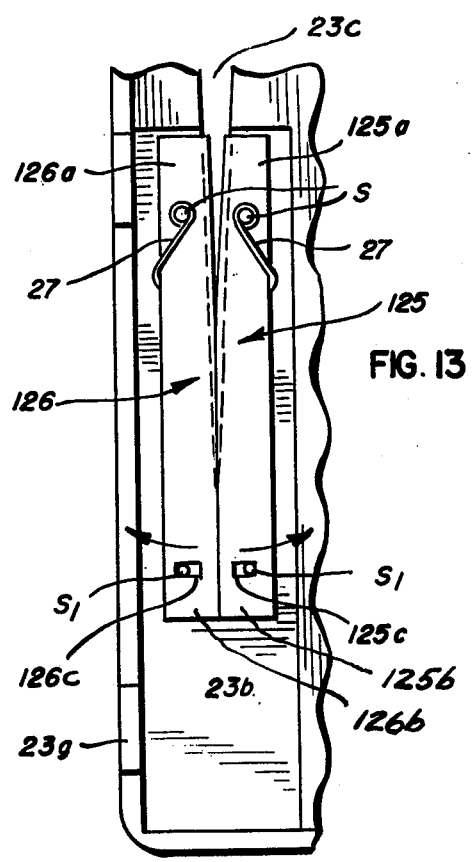

TOOL CLEANING DEVICE

BACKGROUND OF THE INVENTION

During the course of performing surgery, instruments, such as knifes or the like, when used will frequently become soiled with particles of tissue or the like adhering to the exterior of the blade. Unless such particles are removed therefrom within a short period of time after the blade becomes soiled, difficulty will be encountered in sterilizing the tool at some subsequent time because of the adhesion developed between the blade surface and the particle. Oftentimes to avoid this problem the blade is cleaned by wiping it with a disposable piece of gauze or the like. Such a manipulation, however, normally requires both hands of the surgeon, his assistant or attendant. During wiping of the soiled blade extreme care must be exercised so that the person performing the wiping manipulation is not accidentally cut or injured. Furthermore, such a procedure requires that a significant supply of gauze sheets be maintained at a readily accessible location while the surgery is being performed. In certain instances this might present a space problem or restrict the movements of those involved in performing the surgery. Properly disposing of the soiled wiping sheets may become an awkward and frustrating project.

SUMMARY OF THE INVENTION

Thus, it is an object of the invention to provide a simple, inexpensive device which will effectively remove particles of tissue or the like from a soiled segment of a surgical tool without requiring the use of both hands of the person utilizing the device.

It is a further object of the invention to provide a cleaning device which is compact and sturdy and may be readily positioned in an accessible location without obstructing or interfering with the surgeon or others during performance of the surgery.

It is a still further object of the invention to provide a single cleaning device which is capable of being used repeatedly during the course of surgery and then may be readily disposed of at the conclusion of the surgery.

It is a still further object of the invention to provide a cleaning device which requires only one hand to perform the cleaning operation.

It is a still further object of the invention to provide a cleaning device which avoids the hands of the person utilizing the device from coming into contact with the soiled segment of the tool being cleaned.

It is a further object of the invention to provide a cleaning device which is capable of accommodating tools having sizes and configurations varying over a wide range.

Further and additional objects will appear from the description, accompanying drawings and appended claims.

In accordance with one embodiment of the invention, a device is provided for use in cleaning a soiled segment of a tool, such as surgical knife or the like. The device includes a hollow casing having an elongated slot formed in an exterior surface portion thereof. Disposed within the casing is a setose member having the setae thereof of resilient construction and aligned with the casing slot. The casing slot is adapted to have the soiled segment of a tool inserted therethrough and then moved longitudinally of the slot whereupon the setae will frictionally engage the soiled segment and effect cleaning thereof.

DESCRIPTION

For a more complete understanding of the invention, reference should be made to the drawings wherein:

FIG. 1 is a perspective top view of one form of the cleaning device and showing an end segment of a tool disposed within one of the slots formed in a portion of the casing exterior surface.

FIG. 2 is a perspective top view of the device of FIG. 1 and showing the components thereof in exploded relation.

FIG. 3 is a top plan view of the device of FIG. 1.

FIG. 4 is an enlarged, fragmentary sectional view taken along line 4—4 of FIG. 3.

FIG. 5 is a fragmentary bottom view of the device of FIG. 1 with portions of the casing and setose member thereof removed so as to expose the concealed side of the slotted surface portion of the casing.

FIG. 9 is similar to FIG. 3 but showing a third form of the cleaning device.

FIG. 10 is an enlarged, fragmentary top plan view of the setose member embodied in the device of FIG. 9.

FIG. 11 is an enlarged, fragmentary sectional view taken along line 11—11 of FIG. 10.

FIG. 12 is similar to FIG. 10 but showing a modified form of the setose member.

FIG. 13 is an enlarged, fragmentary view similar to FIG. 5 but showing a modified arrangement at the trailing end portion of a casing slot.

Figure 6:
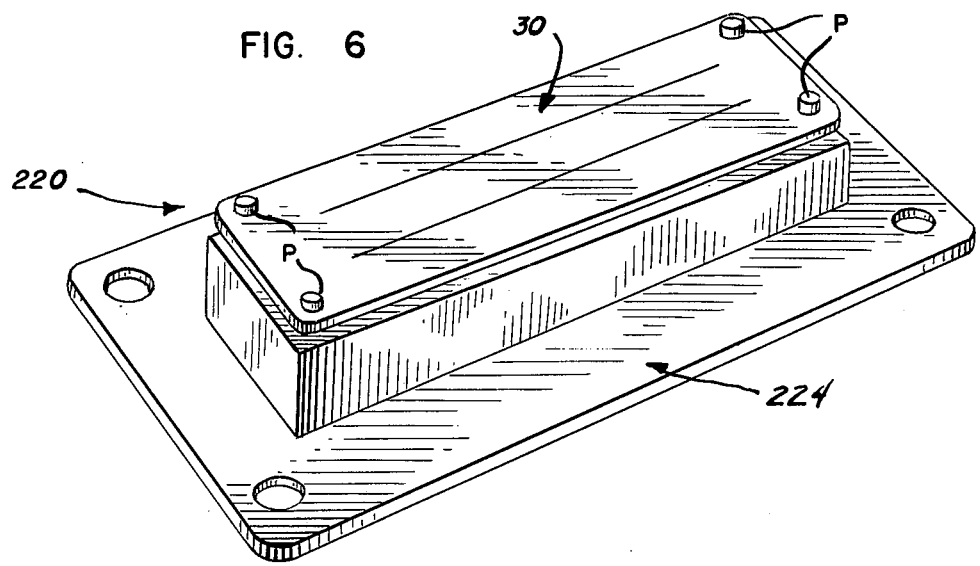
FIG. 6 is similar to FIG. 1 but showing a second form of the cleaning device.

Referring now to the drawings and more particularly to FIGS. 1-3, a preferred embodiment of the cleaning device 20 is shown which is adapted to be used in cleaning a soiled end portion E of a tool T (e.g. a surgical knife).

In performing surgery it frequently occurs that the blades of knifes used become soiled with particles of tissues adhering to the exterior surface thereof. It is important that the tissue particles be removed as soon as possible from the soiled blade so that subsequent sterilization of the tool will be facilitated.

The device 20 as seen in FIG. 1 includes a casing 21, preferably formed of an inexpensive, semi-rigid, plastic material (e.g. Melamine resin), and a setose member 22 disposed within the casing. As seen more clearly in FIG. 2, casing 21 includes an elongated cover section 23 and a base section 24. Cover section 23 in the illustrated embodiment is of rectangular configuration with the bottom 23a thereof open. The elongated top 23b of the cover section 23 has a planar exterior surface, which is provided with a pair of elongated slots 23c and 23d, the longitudinal axes of which are disposed in substantially parallel relation with the longitudinal axis X—X of the top exterior surface, see FIG. 3. Each slot may be of like configuration and is provided with an enlarged head end portion H at which point the soiled end E of the tool is initially inserted into the slot. The rear end portion R of the slot has a narrow tapered configuration and is where the inserted tool end E is withdrawn from the slot subsequent to having been moved longitudinally thereof.

The top 23b of the cover section 23 is delimited by depending side walls 23e and end walls 23f. As seen in FIG. 3, the lower edges of the side walls 23e may be provided with a plurality of lugs 23g which are adapted to interfit with a corresponding number of openings 24a formed in the base section 24, when the casing sections 23, 24 are assembled. Base section 24 is preferably of planar configuration and when assembled with cover section 23 has a marginal portion 24b thereof which extends laterally outwardly a substantial distance beyond the depending side and end walls 23e, 23f, respectively, of the cover section 23. The size of the base section relative to the cover section provides stability for the device when the latter is resting upon a table or counter top. Apertures 24c may be provided in the corners of the marginal portion 24b to facilitate clamping or pinning of the device onto a cover sheet, or a gown worn by the patient.

The setose member 22 preferably has a shape which conforms substantially to the configuration of the interior compartment of the cover section 23 in which the member 22 is placed when the various components of the device are assembled. Member 22 includes a base panel 22a which is shaped so as to fit snugly within the cover section, see FIG. 4. Extending upwardly from the panel 22a are a plurality of setae, or pin-like elements, 22b. The setae are disposed in spaced parallel relation and are arranged in parallel rows, with successive rows having the setae thereof in either staggered (FIG. 10) or aligned (FIG. 12) relation. The setae 22b are preferably formed of hardened, yet resilient wire whereby certain of the setae will frictionally engage the exterior surfaces of the inserted tool end E, when the latter is moved longitudinally of the slot. As seen in FIG. 4, a pair of adjacent setae 22b have the lower ends thereof interconnected by a bail portion 22c. If desired, the setose member 22 may be adhesively secured to the base section 24.

To ensure proper stripping of the adhered tissue particles from the exterior of the inserted tool end E, a pair of elongated bladelike elements 25 and 26 may be mounted on the underside of the top 23b of the cover section 23 adjacent the rear end portion R of at least one of the slots. The elements 25 and 26 are held in proper relative position by locating pins 23h formed on the underside of the top 23b, see FIG. 5. The forward ends 25a and 26a of the elements project a slight amount into the slot and define a somewhat restrictive opening into which the tool end is guided. The adjacent edges of the elements forming the restrictive opening are sharpened and hardened so as to retain their sharpness notwithstanding repeated engagement with a tool end. The rear portions 25b and 26b of the elements are retained in abutting relation, see FIG. 5.

In a modified construction, shown in FIG. 13, the rear portions 125b and 126b of the elements 125 and 126 are retained in a resilient abutting relation and are moved to a non-abutting relation, not shown, by the inserted tool end E being moved therebetween. To permit such relative movement, the forward ends 125a and 126a of the elements are adapted to pivot in opposite directions a slight amount about locating studs S formed on the underside of the top surface 23b of the cover section 23. Similar studs S' are provided adjacent the rear portions 125b, 126b of the elements which extend through enlarged openings 125c, 126c formed in the elements. To maintain proper resilient abutting relation, conventional coil springs 27 may be utilized which engage the studs S.

While the slots 23c and 23d in the device 20 are shown in FIG. 3 to be disposed in substantially parallel relation with the longitudinal axis X—X of the cover section 23, the arrangement of the slots may be varied so that they are disposed at a slight angle (e.g. 5°) to the axis X—X, as seen in FIG. 9. In this latter arrangement, greater frictional engagement between the setae 22b and the inserted end E of the tool may occur as the tool end is moved longitudinally of the slot.

Figure 7:
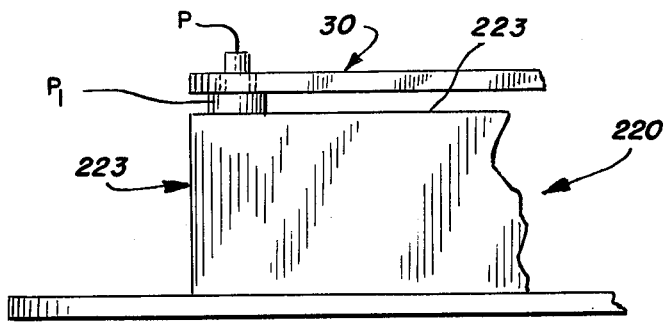
FIG. 7 is an enlarged, fragmentary side elevational view of the device of FIG. 6.
Figure 8:
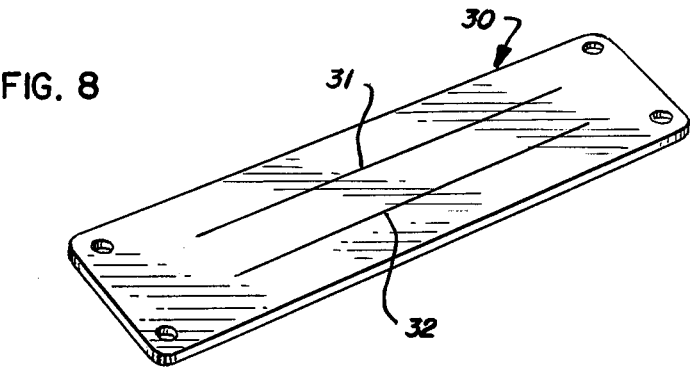
FIG. 8 is a perspective top view of a shield piece per se comprising a component of the device of FIG. 6.

FIGS. 6–8 disclose a shield piece 30 which may be utilized with a device 220 having a structure substantially the same as device 20. Shield piece 30 is mounted in spaced superimposed relation on the slotted top surface 223b of the cover section 223 of the casing 221. The shield piece is formed from a thin sheet of semi-flexible, or yieldable, inexpensive plastic material. The piece is held in place by corner posts P which project upwardly from the surface 223b. A shoulder P' is formed in each post and coacts with the piece to hold same in spaced relation relative to the top surface of the cover section 223, see FIG. 7. The shield piece is provided with a pair of narrow, elongated slits 31, 32 which are aligned and coextensive with the slots formed in the top surface 223b of the cover section 223. The slits are sized to permit the soiled end of the tool to pass therethrough into the slot positioned therebeneath. The function of shield piece 30 is to prevent splattering of the tissue particles as they are being removed from the soiled tool end E by the resilient setae 22b. While the slits 31 and 32 may be narrower than the thickness of the tool end E, the portions of the shield piece adjacent the slits will readily distort to allow the tool end to pass therethrough.

Thus, it will be seen that a simple, inexpensive, yet effective device has been provided which will clean a soiled end of a tool without both hands of the operator being required to manipulate the device. The device eliminates the danger of an operator being injured when the soiled end of the tool is being cleaned. The cleaning device eliminates the need for maintaining a supply of cleaning gauze or tissue.

We claim:

1. A tool cleaning device comprising a hollow casing having a generally planar, substantially inflexible exterior surface portion provided with an elongated slot having an enlarged first end into which a soiled segment of the tool is adapted to be inserted, and a narrow end from which the inserted segment of tool is adapted to be withdrawn subsequent to being cleaned, the ends of the slot being interconnected by elongated substantially inflexible sides converging from the enlarged end to the narrow end so as to provide a tapered configuration to said narrow end, and an elongated setose member disposed in a substantially fixed position within said casing and having elongated resilient setae thereof disposed with their axes substantially normal to the generally planar exterior surface portion of said casing, said setae having the free ends thereof adjacent said slot and adapted to frictionally tangentially engage and clean opposing side surfaces of the inserted tool segment upon relative movement of the latter longitudinally of the slot and the narrow end thereof adapted to effect cleaning along the sides of said tool upon withdrawal thereof from said slot.

2. The device of claim 1 wherein the portions of the casing juxtaposed opposite sides of the narrow tapered end of the slot are provided with reinforcing means.

3. The device of claim 2 wherein the reinforcing means includes a pair of elongated bladelike elements mounted in substantially coplanar relation on the opposing sides of the slot and having peripheral portions of each element protruding into said slot.

4. The device of claim 3 wherein the end portions of said bladelike elements remote from the enlarged end of the slot are disposed in resilient abutting relation and are movable into a non-abutting relation by the tool segment when the latter is moved to the narrow end of the slot.

* * * * *